United States Patent [19]
Martin et al.

[11] Patent Number: 5,078,990
[45] Date of Patent: Jan. 7, 1992

[54] SHAMPOOS AND CONDITIONING SHAMPOOS HAVING INCREASED CAPACITY FOR INCORPORATION OF CONDITIONING AGENTS AND REMOVAL OF HAIR SOIL

[75] Inventors: Kathleen Martin, Oak Park; Priscilla L. Walling, Darien, both of Ill.

[73] Assignee: Helene Curtis, Inc., Chicago, Ill.

[21] Appl. No.: 552,432

[22] Filed: Jul. 13, 1990

[51] Int. Cl.$^5$ .............................. A61K 7/075
[52] U.S. Cl. ..................... 424/70; 252/174.15; 252/550; 252/547; 252/DIG. 13
[58] Field of Search ............... 424/70, 178; 252/DIG. 13, 547, 550, 174.15, 551

[56] References Cited

U.S. PATENT DOCUMENTS

| | | | |
|---|---|---|---|
| 2,826,551 | 3/1958 | Green | 252/DIG. 14 |
| 3,822,312 | 7/1974 | Sato et al. | 424/70 X |
| 3,849,348 | 11/1974 | Hewitt | 252/DIG. 13 |
| 3,964,500 | 6/1976 | Drakoff | 424/70 X |
| 3,990,991 | 11/1976 | Gerstein | 424/70 X |
| 4,364,837 | 12/1982 | Pader | 424/70 X |
| 4,704,272 | 11/1987 | Oh et al. | 424/70 |
| 4,728,457 | 3/1988 | Fieler et al. | 252/547 X |
| 4,741,855 | 5/1988 | Grote et al. | 424/70 X |
| 4,788,006 | 11/1988 | Bolich, Jr. et al. | 252/DIG. 2 |
| 4,830,774 | 5/1989 | La Petina et al. | 252/171.24 |
| 4,902,499 | 2/1990 | Bolich, Jr. et al. | 252/DIG. 13 |

Primary Examiner—Thurman K. Page
Assistant Examiner—Susan S. Rucker
Attorney, Agent, or Firm—Marshall, O'Toole Gerstein, Murray & Bicknell

[57] ABSTRACT

An aqueous shampoo containing a long chain alkyl sulfate and/or long chain alkyl ether sulfate anionic surfactant, and a cationic di-long chain alkyl quaternary ammonium nitrogen-containing compound, unexpectedly increases the ability of the aqueous shampoo (1) to incorporate water-insoluble conditioning agents, particularly non-volatile silicone materials, and (2) to remove previously applied conditioning agents and other soiled conditioning agents and contaminants from the hair.

20 Claims, 4 Drawing Sheets

SHAMPOOS AND CONDITIONING SHAMPOOS HAVING INCREASED CAPACITY FOR INCORPORATION OF CONDITIONING AGENTS AND REMOVAL OF HAIR SOIL

FIELD OF THE INVENTION

The present invention is directed to a composition and method capable of incorporating or "solubilizing" unexpectedly high amounts of conditioning agents, such as hydrocarbons, including long chain hydrocarbons, and silicones; and removal of oils, greases, soils, conditioning agents and the like from the hair. More particularly, the present invention is directed to a shampoo composition and a hair conditioning shampoo composition and to a method of treating hair with the compositions to cleanse the hair. In a conditioning shampoo embodiment, the hair is provided with unexpectedly improved wet stage and dry stage conditioning properties as well as other conditioning properties, such as softness, without residual build-up of conditioning agents on the hair. More particularly, the present invention is directed to a hair conditioning shampoo composition including one or more anionic cleaning surfactants, selected from the group consisting of long chain alkyl sulfates and long chain alkyl ether sulfates and mixtures including the partially ethoxylated long chain alkyl sulfates; and a water-insoluble, oil-soluble di-long chain alkyl quaternary ammonium nitrogen-containing compounds in water that act synergistically to increase the degree of incorporation or "solubility" of conditioning agents, such as volatile hydrocarbons and non-volatile silicone oils and gums, such as polydimethylsiloxane compounds. The anionic surfactant/cationic di-long chain alkyl quaternary ammonium nitrogen-containing compounds are compatible, and synergistically combine, particularly at temperatures above about 30° C., especially at about 35° C. to about 40° C. for unexpected incorporation or "solubilization" of conditioning agents, such as silicones and volatile hydrocarbons and for removal of soils and the like from the hair. The increased "solubility" permits the incorporation of unexpectedly high amounts of volatile hydrocarbons, silicones and other conditioning agents into a conditioning shampoo composition and permits unexpectedly increased "solubilization" and removal of dirt, grease, soil, oils and the like from the hair at normal washing temperatures of about 30° C. to about 50° C., particularly about 35° C. to about 45° C.

BACKGROUND OF THE INVENTION AND PRIOR ART

Soiled human hair is shampooed to remove sebum that is naturally secreted by the head as well as soil and other atmospheric contaminants that accumulate on the hair. Sebum, in particular, accumulates on the hair in a relatively short period of time leaving the hair with a greasy, dirty feel and poor manageability. The most effective shampoos for cleansing the hair for removal of the atmospheric contaminants and sebum, are those that contain high lather synthetic anionic detergents, such as the long chain alkyl sulfates and the partially ethoxylated long chain alkyl sulfates. These synthetic anionic detergents are very effective for cleansing the hair but, after rinsing with water, leave the hair with a dried touch, usually called "creak" and result in hair, when wet, that is in an extremely tangled and unmanageable after-shampoo condition.

Thoroughly cleansed hair is extremely difficult to comb, in either the wet or dry state because the individual hair fibers tend to snarl, kink, and interlock with each other. Particularly prior to complete drying of thoroughly cleansed hair, in this after-shampoo stage, the hair is very difficult to comb or brush. Even after complete drying, the thoroughly cleansed hair remains difficult to comb or brush and does not set well. Thoroughly clean, dried hair also has undesirable electrostatic properties in a low humidity atmosphere that causes the hair to "fly away", thereby further reducing the combing or brushing property of the hair. Generally, these above-outlined problems that result from synthetic detergent cleansing of the hair, particularly the high-lather synthetic anionic detergents, have been alleviated either by the after-shampoo treatment of the hair with hair conditioners, for example in the form of a hair rinse, or by including hair conditioners directly within the shampoo composition.

After-shampoo hair conditioning compositions are easily formulated but are inconvenient to use because of the necessity of applying the conditioner to the hair in a separate stage, after shampooing. The preparation of a conditioning shampoo has been more difficult because of inherent incompatibility problems between anionic surfactants and the fatty cationic compounds that are good conditioning agents. Contact between an anionic surfactant and a cationic surfactant or cationic polymer produces a precipitate that forms immediately or causes an interaction between the anionic and cationic compounds that significantly reduces their respective cleaning and conditioning properties. The reduction in cleansing and conditioning effectiveness is observed even in compositions wherein the anionic and cationic compounds do not precipitate from the composition but remain in solution or suspension. This incompatibility between an anionic surfactant and a cationic conditioning compound is well recognized by those skilled in the art. For example, Sagarin in *Cosmetics*, Interscience Publishers, Inc., New York, p. 538 (1957), states that anionic and cationic compounds cannot be used in combination because they react to form insoluble salts.

A partial solution to this incompatibility problem in the formulation of conditioning shampoos is exemplified by the following patents that disclose compositions that contain surfactants that are not anionic e.g. non-ionics, amphoterics and zwitterionics together with cationic conditioning compounds: U.S. Pat. No. 3,849,348 to Hewitt; U.S. Pat. No. 3,990,991 to Gerstein; and U.S. Pat. No. 3,822,312 to Sato.

Another problem inherent in formulating a conditioning shampoo is an instability problem that results when water-insoluble conditioning agents are also included in the conditioning shampoo composition, such as the non-volatile silicones that are well recognized in the art as providing a degree of softness to the hair.

Silicones in shampoo compositions have been disclosed in a number of different patents: U.S. Pat. No. 2,826,551, Mar. 11, 1958 to Green; U.S. Pat. No. 3,964,500, June 22, 1976 to Drakoff; U.S. Pat. No. 4,364,837, Dec. 21, 1982 to Pader; British Pat. No. 849,433, Sept 28, 1960 to Woolston; U.S. Pat. No. 4,741,855 to Grote, et al.; U.S. Pat. Nos. 4,788,006 and 4,902,499 to Bolich, Jr. et al. and U.S. Pat. No. 4,704,272 to Oh et al.

A particularly difficult problem to solve in silicone-containing conditioning shampoos is that of keeping a dispersed, insoluble, non-volatile silicone material suspended in stable form while retaining the cleansing and conditioning performance of the conditioning shampoo. The stability problem is particularly prevalent in conditioning shampoos like those disclosed herein containing an anionic surfactant and a cationic conditioning material which, as outlined above, by themselves tend to interact and present stability problems. A variety of materials have been proposed for inclusion in silicone-containing conditioning shampoos for purposes of thickening and stabilization such as xanthan gum, long chain acyl derivatives, long chain amide oxides, and long chain alkanolamides as disclosed in U.S. Pat. Nos. 4,788,006; 4,704,272; and 4,741,855.

In accordance with the present invention, it has been found that water-insoluble di-long chain quaternary ammonium compounds, particularly dioctadecyl ammonium salts, e.g. dioctadecyldimethyl ammonium chloride, cooperate unexpectedly with long chain alkyl sulfates and partially ethoxylated long chain alkyl sulfates, particularly ammonium lauryl sulfate and ammonium lauryl ether sulfate, when the molar ratio of long chain alkyl sulfate and/or long chain alkyl ether sulfate to di-long chain quaternary ammonium compound is at least about 85:1. To achieve the full advantage of the present invention, the molar ratio of alkyl sulfate and/or long chain alkyl ether sulfate to di-long chain quaternary ammonium compound should be at least 100:1, particularly about 100:1 to about 150:1, and up to about 1000:1. At this high ratio of strong anionic detergent to cationic quaternary ammonium compound, essentially no precipitation occurs as a result of the electrostatic interaction between the strongly anionic detergents and the cationic quaternary ammonium compound, but such high ratios have not been used because of the negligible conditioning advantage imparted by the small amount of cationic quaternary ammonium compound.

Surprisingly, it has been found, however, that the unusually high ratio of long chain alkyl sulfate and/or long chain alkyl ether sulfate to di-long chain quaternary ammonium compound lowers the infrared stretching frequency of $CH_2$ groups in the anionic long chain detergent hydrocarbon chains that are freely moving (as in a liquid) as the temperature is increased to about 30° C. or above. This lowering of stretching frequency at higher temperature is quite unusual since higher temperature normally induces more disorder in a molecule causing the $CH_2$ stretching to shift to a higher frequency at the higher temperatures. Quite surprisingly, this lower frequency CH2 stretching band at higher temperatures, particularly in the range of about 30° C. to about 50° C. reflects the ability of the compositions of the present invention to incorporate or "solubilize", and/or remove from the hair, various hydrocarbon materials such as conditioning agents, e.g. silicones, long chain hydrocarbons, soil, sebum, dirt and the like. This ability to incorporate or "solubilize" and/or remove these and other compounds in unexpected amounts is due to the interaction between the strongly anionic long chain alkyl sulfate detergents and the di-long chain quaternary ammonium compounds at molar ratios of at least 85:1 sulfate and/or ether sulfate to quat that creates more order to the $CH_2$—containing long chain alkyl sulfate and/or alkyl ether sulfate molecules for easier incorporation of materials into the composition and/or removal of materials from the hair. This unexpected increased order to the alkyl sulfate and/or alkyl ether sulfate molecules, at higher temperatures permits conditioning agents and contaminant molecules to be removed easily from the hair at normal hair washing temperatures, e.g. about 30° C. to about 50° C., and permits the incorporation of unexpectedly increased amounts of volatile, non-volatile and rigid silicones and other conditioning agents into the aqueous shampoo compositions.

It should be understood that the use of the terms "solubilize" and "solubilization" as used herein in reference to the ability of the compositions of the present invention to form a stable conditioning shampoo composition or to remove a material from the hair, is not limited to the formation of a true solution of the material in water but used in the broader sense of the capability of forming a functional (in the sense of incorporating or removing) mixture of the material with water as either a stable composition (incorporating) or a mixture of the material with water such that the material can be removed from the hair (removing).

SUMMARY OF THE INVENTION

In accordance with the principles of the present invention, it has been found, surprisingly, that an aqueous shampoo containing a long chain alkyl sulfate and/or long chain alkyl ether sulfate anionic surfactant, and a cationic di-long chain alkyl quaternary ammonium nitrogen-containing compound, unexpectedly increases the ability of the aqueous shampoo 1) to incorporate water-insoluble conditioning agents, particularly non-volatile silicone materials, and 2) to remove previously applied conditioning agents and other soiled conditioning agents and contaminants from the hair. The aqueous shampoos of the present invention have extended product stability, excellent cleansing properties and, when conditioning agent(s) are included in the shampoo, provide unexpected overall conditioning to human hair, and particularly superior wet and dry combing properties. Further, the shampoos have unexpectedly increased capacity to dissolve and remove dirt, sebum, silicones and other hydrocarbon build-ups from the hair when shampooed with the compositions at a temperature of at least about 30° C.

One of the problems inherent with conditioning shampoos is that the conditioning agent must be retained on the hair after rinsing in order to impart the desired conditioning properties to the hair. Between shampoos, the conditioning agent, as well as the hair, contacts a number of natural and environmental contaminants such as sebum, dirt, smoke and the like, and the conditioning agent, as well as the hair, becomes contaminated. A conditioning shampoo capable of substantially complete removal of the contaminated conditioning agent left on the hair from one or more previous conditioning shampoo treatments and capable of conditioning the hair with fresh, non-contaminated conditioning agent has not been possible prior to the present invention except from separate applications of shampoo and conditioner.

It has been a long felt need in this art to provide a shampoo that has an unexpectedly increased capacity to remove contaminants and conditioning agents from hair at normal shampooing temperatures of about 30° C. to about 50° C. It has also been a long felt need in this art to find a conditioning shampoo that has an unexpectedly increased capacity to remove contaminants and conditioning agents from the hair as well as an unexpectedly increased capacity to remove previously applied hydrocarbon materials and other contaminants from the hair, while retaining the capability of conditioning the hair, in a single conditioning shampoo composition using a single application. The shampoos and conditioning shampoos of the present invention solve these long felt needs in this art. The compositions of the present invention can be formulated as shampoos, including only a small amount of di-long chain quaternary ammonium nitrogen-containing compound, insufficient to provide any substantial conditioning to the hair; or the compositions can be formulated to include an effective amount of about 0.5% about 10% by weight of one or more conditioning agents other than a dioctadecyl quaternary ammonium salt compound, particularly a substantial amount of non-volatile silicone oils and/or gums.

Compositions of the present invention are stable and do not exhibit the inherent anionic surfactant/ cationic conditioning agent incompatibility at the low levels of cationic di-long chain quaternary ammonium compound contained therein. This feature is not surprising at such low cationic levels. However, it was surprisingly and unexpectedly found that hair treated with the compositions of the present invention is thoroughly cleansed and, when the composition also contains an effective amount of a conditioning agent, particularly water-insoluble (e.g. less than about 1% by weight water soluble) conditioning agents, such as volatile hydrocarbons, silicone oils and/or silicone gums, the hair exhibits improved physical and cosmetic properties, such as gloss, thickness, manageability, softness and body. Further, it was surprisingly and unexpectedly found that hair treated with the conditioning shampoo compositions of the present invention is capable of essentially complete prevention of conditioning agent build-up on the hair shaft, over time, as is common with many conditioning shampoo compositions.

Therefore, an aspect of the present invention is to provide a hair-treating shampoo composition that cleanses the hair and substantially completely removes conditioning agents and other hydrocarbon soils and contaminants from the hair.

Another aspect of the present invention is to provide a new and improved conditioning shampoo that simultaneously removes soiled conditioning agents substantially completely from the hair while depositing fresh, unsoiled conditioning agent onto the hair.

Another aspect of the present invention is to provide a physically stable conditioning shampoo containing an anionic surfactant, a cationic conditioning agent, and a non-volatile silicone material.

Another aspect of the present invention is to provide a new and improved conditioning shampoo containing a long chain alkyl sulfate, long chain alkyl ether sulfate, and/or mixtures; that is compatible with a very low molar ratio of a di-long chain cationic quaternary ammonium nitrogen-containing compound; and a non-volatile silicone conditioning agent, that has an unexpected capacity to incorporate high levels of nonvolatile silicone conditioning agent.

Still another aspect of the present invention is to provide a new and improved aqueous shampoo including a long chain ammonium alkyl sulfate, and/or a long chain ammonium alkyl ether sulfate; together with a di-long chain quaternary ammonium nitrogen-containing compound in a molar ratio of alkyl sulfate and/or alkyl ether sulfate to quaternary ammonium compound of at least about 85 to 1, that has an unexpectedly high capacity for incorporating water-insoluble conditioning agents therein.

Another aspect of the present invention is to provide a new and improved aqueous shampoo including a long chain alkyl sulfate and/or long chain alkyl ether sulfate together with a di-long chain quaternary ammonium compound in a molar ratio of alkyl sulfate and/or alkyl ether sulfate to quaternary ammonium compound of at least about 85 to 1, that has an unexpectedly increased capacity to remove soil, sebum, conditioning agents and hydrocarbonaceous contaminants from hair at rinse water temperatures in the range of about 30° C. to about 50° C., particularly about 35° C. to about 45° C.

The above and other aspects and advantages of the present invention will become apparent from the following detailed description of the preferred embodiments.

DETAILED DESCRIPTION OF THE PREFERRED EMBODIMENTS

The aqueous shampoo and conditioning shampoo compositions of the present invention generally include an anionic surfactant selected from the group consisting of a long chain alkyl sulfate and/or a long chain alkyl ether sulfate in an amount of about 5% to about 65% by weight of the composition; a cationic di-long chain alkyl quaternary ammonium nitrogen-containing compound in a molar amount of alkyl sulfate and/or alkyl ether sulfate, in relation to the molar amount of quaternary ammonium nitrogen-containing compound, of at least 85 moles of anionic surfactant per mole of the di-long chain quaternary ammonium nitrogen-containing compound; and, optionally, one or more volatile hydrocarbons, nonvolatile silicones or other conditioning agents in an amount of about 0.5% to about 10% by weight of the composition.

The conditioning shampoos of the present invention provide the hair with improved physical and cosmetic conditioning properties, such as gloss, thickness, softness, and manageability, including excellent wet and dry combing properties and body. It is surprising and unexpected that the composition of the present invention, including a long chain anionic cleansing surfactant; and a cationic di-long chain alkyl quaternary ammonium nitrogen-containing compound; and, optionally, a conditioning agent, such as a non-volatile silicone material, remains stable, while achieving excellent cleansing and conditioning and "solubilization" (within the composition and from the hair) of conditioning agents, hydrocarbonaceous materials, and soils, greases, oils and other hair contaminants.

The anionic cleansing surfactants included in the composition and method of the present invention can be any of the anionic surfactants known or previously used in the art of hair shampoos. An anionic cleansing surfactant should be included in the composition of the present invention to effectively cleanse the hair and generates a high, stable foam level that consumers equate with cleaning efficiency. Nonionic and amphoteric surfactants are not as effective in cleansing the hair and do not provide the high foam level desired by consumers. However, optionally, nonionic, amphoteric and/or zwitterionic surfactants can be included in the compositions of the present invention in addition to one or more long chain alkyl sulfate anionic surfactants, to help stabilize foam, to provide a suitable viscosity, or to give other functional or esthetic properties to the composition.

Usually, the anionic cleansing surfactant includes a hydrophobic moiety, such as a carbon chain including from about eight carbon atoms to about 30 carbon atoms, and particularly from about twelve carbon atoms to about twenty carbon atoms and further includes a hydrophilic moiety, such as a sulfate, sulfonate, carbonate, phosphate or carboxylate. Often, the hydrophobic carbon chain is etherified, such as with ethylene oxide or propylene oxide, to impart a particular physical property, such as increased water-solubility or reduced surface tension, to the anionic cleansing surfactant.

Suitable anionic cleansing surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta alkyloxy alkene sulfonates, alkyl arylsulfonates, sulfated monoglycerides, and fatty acid amino polyoxyethylene sulfates; or combinations thereof. Many additional anionic long chain sulfates and ethoxylated sulfates are described in McCUTCHEON'S DETERGENTS and EMULSIFIERS, 1989 ANNUAL published by McCutcheon's Division MC Publishing Company, herein incorporated by reference. Usually, the anionic cleansing surfactant is present in the composition as a neutralized salt in the form of a sodium, potassium, lithium, ammonium, alkylammonium or hydroxyalkylammonium salt, wherein the alkyl moiety includes from one to about three carbon atoms. It has been found that the alkyl sulfates and alkyl ether sulfates are particularly effective classes of anionic cleansing surfactants in combination with the di-long chain quaternary nitrogen compounds, as will be described in more detail hereinafter. Exemplary anionic cleansing surfactants that are useful in the composition and method of the present invention include, but are not limited to, the ammonium, monoethanolamine, diethanolamine, triethanolamine, isopropylamine, sodium, potassium, lithium, or magnesium salts of lauryl sulfate, dodecylbenzenesulfonate, lauryl sulfosuccinate, lauryl ether sulfate, and combinations thereof. An especially useful anionic cleansing surfactant is a mixture of a lauryl sulfate salt and a lauryl ether sulfate salt.

The emulsified conditioning shampoo of the present invention also includes a small molar proportion of a cationic water-insoluble, emulsifiable di-long chain quaternary ammonium nitrogen-containing compound. The di-long chain quaternary ammonium nitrogen-containing compound used in the emulsified conditioning shampoo composition and method of the present invention is an oil-soluble, water-dispersible di-long chain alkyl quaternary ammonium salt, particularly a di-long chain alkyl, di-short chain alkyl quaternary ammonium salt. Oil soluble, water-dispersible quaternary ammonium compounds useful in the composition and method of the present invention are quaternary ammonium compounds having two long chain alkyl groups including from about 12 to about 22 carbon atoms, and particularly the compounds having predominantly (at least 50%) $C_{16}$, $C_{18}$, $C_{20}$ and/or $C_{22}$ alkyl radicals. The long chains can be predominantly 16, 18, 20 and/or 22 carbon atoms in length and can be only one chain length or can be mixed chain lengths. Preferred are the dioctadecyldimethyl ammonium compounds (e.g. chloride or bromide) wherein the di-long chains are at least 75% $C_{18}$ alkyl radicals. The remaining two substitutions present on the quaternary nitrogen of the quaternary ammonium compound can be hydrogen; benzyl; short chain alkyl groups, having 1 to 4 carbon atoms such as methyl, ethyl, or hydroxyethyl; or combinations thereof, as long as the di-long chain quaternary ammonium compound is oil-soluble and water-dispersible and contains two long chain alkyl substitutions, as defined.

The anion of the oil-soluble quaternary ammonium compound can be any anion, such as chloride, bromide, methyl sulfate, acetate, phosphate or nitrate, as long as the quaternary ammonium compound is oil-soluble.

In accordance with an important feature of the present invention, the oil-soluble, water-dispersible di-long chain alkyl quaternary nitrogen-containing compound included in the compositions of the present invention are those having a quaternary nitrogen atom and only two long alkyl chains, having predominantly from about 16 to about 22 carbon atoms, preferably about 18 to about 20 carbon atoms per alkyl chain. These conditioning agents include a wide range of compounds that can be broadly divided into groups based upon the structure of the substitution on the quaternary nitrogen atom, i.e., (a) compounds having two long carbon chains and one or two identical or different short chain alkyl groups having one to four, particularly one or two carbon atoms, and (b) compounds having two long carbon chains, one benzyl group and one short chain alkyl group having one to four, particularly one or two carbon atoms. The following list of oil-soluble quaternary ammonium compounds are exemplary, but not limiting, of oil-soluble, di-long chain alkyl quaternary ammonium compounds that can be used in the compositions and methods of the present invention:

Distearyldimethyl-     (Distearyl dimonium chloride);

| -continued | |
|---|---|
| ammonium chloride | |
| Distearyldimethyl-ammonium bromide | (Distearyl dimonium bromide) |
| Dicetyldimethyl-ammonium bromide | (Dicetyl dimonium bromide); |
| Dimethyldi-(hydrogenated tallow)-ammonium chloride | (Quaternium-18); |
| Dicetylmethylbenzyl-ammonium chloride: | |
| Dicetyldimethyl-ammonium chloride | (Dicetyl dimonium chloride) |
| Dicocodimethyl-ammonium chloride | (Dicoco dimonium chloride) |
| Dicocodimethyl-ammonium bromide | (Dicoco dimonium bromide) |
| Dibehenyl/diarachidyl-dimethyl ammonium chloride | (Dibehenyl/diarachidyl dimonium chloride) |
| Dibehenyl/diarachidyl-dimethyl ammonium bromide | (Dibehenyl/diarachidyl dimonium bromide) |
| Dibehenyl dimonium methyl sulfate | (Dibehenyl dimonium methyl sulfate) |
| Hydroxypropyl bis-stearyl-ammonium chloride | (Hydroxypropyl bis-stearyl dimonium chloride) |
| Dibehenyldimethyl-ammonium chloride; | (Dibehenyl dimonium chloride) |
| Dibehenylmethyl-benzyl-ammonium chloride; | |

Wherein the name in parenthesis is the compound name given in the CTFA Dictionary, Third Edition, 1982.

It should be noted that the long alkyl chains of the oil-soluble quaternary ammonium compound are not commonly of a single chain length, but a mixture of chain lengths primarily within the $C_{12}$–$C_{22}$ range, e.g. $C_{12}$, $C_{14}$, $C_{16}$, $C_{18}$, $C_{20}$ and/or $C_{22}$. Generally, the oil-soluble quaternary ammonium compounds used in the compositions of the present invention have the long alkyl chains as a mixture of alkyl lengths. Such di-long chain alkyl quaternary ammonium compounds function in accordance with the principles of the present invention as long as the quaternary ammonium compound is oil-soluble and water-dispersible and the long alkyl chains are predominantly at least about 16 carbon atoms in length, for each long alkyl radical. For example, a di-long chain alkyl quaternary ammonium compound that has less than 50% myristyl for shorter radicals in the two long chains should function in accordance with the principles of the present invention. Such conditioning agents are prepared conveniently from naturally occurring materials, such as tallow, coconut oil, soya oil and the like, or from synthetically produced mixtures which are known to include a mixture of long chain radicals.

To achieve the full advantage of the present invention, the water-insoluble, emulsifiable di-long chain quaternary ammonium nitrogen-containing compounds used in the compositions of the present invention have a water-solubility of less than one percent. Such agents may be employed either as liquids or as solids.

In accordance with one important (conditioning shampoo) embodiment of the present invention, the composition of the present invention also includes from about 0.5% to about 10%, and preferably from about 1.0% to about 5.0%, by weight of a non-volatile silicone compound or other conditioning agents, preferably a water-insoluble, emulsifiable conditioning agent. The preferred non-volatile silicone compound is a polydimethylsiloxane compound, such as a mixture, in about a 3:1 weight ratio, of a low molecular weight polydimethysiloxane fluid and a higher molecular weight polydimethylsiloxane gum. The non-volatile polydimethylsiloxane compound is added to the composition of the present invention in an amount sufficient to provide improved combing and improved feel (softness) to the hair after shampooing. As referred to herein, "silicone gums" are those nonfunctional siloxanes having a viscosity of from about 5 to about 600,000 centistokes at 25° C. The so-called rigid silicones, as described in U.S. Pat. No. 4,902,499, herein incorporated by reference, having a viscosity above 600,000 centistokes at 20° C., e.g. 700,000 centistokes plus, and a weight average molecular weight of at least about 500,000 also are useful in accordance with the present invention.

Preferred silicone gums include linear and branched polydimethyl siloxanes, of the following general formula:

wherein n is from about 2,000 to about 15,000, preferably from about 2,000 to about 7,000. Silicone gums useful in compositions of the present invention are available from a variety of commercial sources, including General Electric Company and Dow Corning.

Another particularly suitable conditioning agent that can be included in the composition of the present invention is a volatile hydrocarbon, such as a hydrocarbon including from about 10 carbon atoms to about 30 carbon atoms, that has sufficient volatility to slowly volatilize from the hair after application of the conditioning shampoo composition. The volatile hydrocarbons provide essentially the same benefits as the silicone conditioning agents.

The preferred volatile hydrocarbon compound is an aliphatic hydrocarbon including from about 12 to about 24 carbon atoms, and having a boiling point in the range of from about 100° C. to about 300° C. Exemplary volatile hydrocarbons are depicted in general structural formula (I), wherein n ranges from 2 to 5, Examples of volatile hydrocarbons useful in the anhydrous composition of the present invention are the commercially-available compounds PERMETHYL 99A and PERMETHYL 101A, corresponding to compounds of general structure (I) wherein n is 2 and 3, respectively, available from Permethyl Corporation, Frazer, Pa. A volatile hydrocarbon compound is useful in the clear composition of the present invention either alone, in combination with another volatile hydrocarbon, or in combination with a volatile silicone.

Examples of other suitable water-insoluble conditioning agents that can be incorporated into the conditioning shampoos of the present invention include the following: polysiloxane polyether copolymers; polysiloxane polydimethyl dimethylammonium acetate copolymers; acetylated lanolin alcohols; dimethyl dialkyl ammonium chloride; modified alkyl dimethylbenzyl ammonium chloride; lauryl dimethylamine oxide; stearyl dimethyl benzyl ammonium chloride; lanolin-derived extract of sterols and sterol esters; lanolin alcohol concentrate; isopropyl ester of lanolin fatty acids; sulfur rich amino acid concentrate; isopropyl ester of lanolin fatty acids; stearyl dimethyl benzyl ammonium chloride; cetyl trimethyl ammonium chloride; oleyl dimethyl benzyl ammonium chloride; oleyl alcohol; stearyl alcohol; stearyl dimethyl benzyl ammonium chloride; stearamido propyl dimethyl myristyl acetate ammonium chloride; polyol fatty acid; fatty amido amine; guar hydroxypropyltrimonium chloride; cetyl/stearyl alcohol; quaternized protein; keratin protein derivatives; isostearamido propyl dimethylamine; stearamido propyl dimethylamine; myristrimonium bromide; cetrimonium bromide; myrtrimonium bromide; stearalkonium chloride; cetyl trimethyl ammonium chloride; laurylpyridinium chloride; tris (oligoxyethyl) alkyl ammonium phosphate; amino functional silicones; lapyrium chloride; isopropyl ester of lanolic acids; ethoxylated (30) castor oil; acetylated lanolin alcohol; fatty alcohol fraction of lanolin; mineral oil and lanolin alcohol mixture; high m. w, esters of lanolin; quaternium-75; vinylpyrrolidone/dimethylaminoethylmethacrylate copolymer; alkyl trimethyl ammonium chloride; 5 mole ethylene oxide adduct of soya sterol; 10 mole ethylene oxide adduct of soya sterol; stearic acid ester of ethoxylated (20 mole) methyl glucoside; sodium salt of polyhydroxycarboxylic acid; hydroxylated lanolin; cocamidopropyl dimethylamine lactate; cocamidopropyl dimethylamine propionate; cocamidopropyl morpholine lactate; isostearamidopropyl dimethylamine lactate; isostearamidopropyl morpholine lactate; oleamidopropyl dimethylamine lactate; linoleamidopropyl dimethylamine lactate; stearamidopropyl dimethylamine lactate, ethylene glycol monostearate and propylene glycol mixture; stearamidopropyl dimethylamine lactate; acetamide MEA; lactamide MEA; stearamide MEA; behanalkonium chloride; behenyl trimethyl ammonium methosulfate and cetearyl alcohol mixture; cetearyl alcohol; isostearamidopropalkonium chloride; linoleamidopropalkonium chloride; oleyl dimethyl benzyl ammonium chloride; tallow imidazolinum methosulfate; stearyl dimethyl benzyl ammonium chloride; stearyl trimonium methosulfate; mixed ethoxylated & propoxylated long chain alcohols; stearamidopropyl dimethylamine lactate; polonitomine oxide; oleamine oxide; stearamine oxide;soya ethyldimonium ethosulfate; anhydroxypropyl bislauryl-dimonium chloride; hydroxypropyl biscetyldimonium chloride; hydroxypropyl bisstearyl dimonium chloride; hydroxypropyl bisbehenyl dimonium chloride; ricinolamido propyl ethyldimonium ethosulfate; olealkonium chloride; stearalkonium chloride; N-(3-Isostearamido propyl)-N,N-dimethyl amino glycolate; N(3-Isostearamido propyl)-N,N dimethyl amino gluconate; hydrolyzed animal keratin; ethyl hydrolyzed animal keratin; stearyl ammonium chloride; stearamidoethyl diethylamine; cocamidopropyl dimethylamine; lauramidopropyl dimethylamine; oleamidopropyl dimethylamine; palmitamidopropyl dimethylamine; stearamidopropyl dimethylamine lcictate; avocado oil; sweet almond oil, grape seed oil; jojoba oil; apricot kernel oil; sesame oil; hybrid safflower oil; wheat germ oil; cocamidoamine lactate; ricinoleamido amine lactate; stearamido amine lactate; stearamido morpholine lactate; isostearamido amine lactate; isostearamido morpholine lactate; wheat germanido-dimethylamine lactate; behenamido-propyl betaine; ricinoleamidopropyl betaine; wheat germamido propyl dimethylamine oxide; disodium isostearaimido MEA sulfosuccinate; disodium oleamide PEG-2 sulfosuccinate; disodium oleamide MEA sulfosuccinate; disodium ricinoleyl MEA sulfosuccinate; disodium wheat germ-amido, MEA sulfo-succinate; disodium wheat germido PEG-2 sulfosuccinate; stearalkonium chloride; stearly dimethyl benzyl ammonium chloride; stearamido amine; stearamido morpholine; isostearamido amine; isostearamido morpholine; polyethyleneglycol (400) mono and distearates; synthetic calcium silicate; isostearic alkanolamide; ethyl esters of hydrolyzed animal protein; blend of cetyl, stearyl alcohols with ethoxylated cetyl or stearyl alcohols; amido amines; polyamido amines; palmetyl amido betaine; propoxylated (1-20 moles) lanolin alcohols; isostearamide DEA; and hydrolyzed collagen protein.

When one or more of these water-insoluble conditioning agents is included in the composition of the present invention to form a conditioning shampoo, in an amount of about 0.5% to about 10% by total weight of the composition, the composition also should include a suspending agent for the conditioning agent, in an amount of about 0.5% to about 10%, by total weight of the composition. The particular suspending agent is not critical and can be selected from any materials known to suspend water-insoluble liquids in shampoo compositions. Suitable suspending agents are for example, distearyl amate (distearyl phthalamic acid); fatty acid alkanolamides; esters of polyols and sugars; polyethylene glycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in the literature, such as McCUTCHEON'S DETERGENTS AND EMULSIFIERS, 1989 Annual, published by McCutcheon Division, MC Publishing Co.

To achieve the full advantage of the conditioning shampoo embodiment of the present invention, a non-ionic alkanolamide is included in the conditioning shampoo composition in an amount of about 0.1% to about 5% by weight to provide exceptionally stable emulsification of water-insoluble conditioning agents and to aid in thickening and foam stability. Other useful suspending and thickening agents can be used instead of the alkanolamides such as sodium alginate; guar gum; xanthan gum; gum arabic, cellulose derivatives, such as methylcellulose, hydroxybutylcellulose, hydroxyethylcellulose, hydroxypropylcellulose and carboxymethylcellulose,; and various synthetic polymeric thickeners, such as the polyacrylic acid derivatives. Suitable alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof. Other suitable suspending agents are disclosed in Oh et al. U.S. Pat. No. 4,704,272; Grote et al. U.S. Pat. No. 4,741,855; and Bolich, Jr. et al. U.S. Pat. No. 4,788,006, which patents are hereby incorporated by reference.

Suitable polymeric suspending agents can be cationic, anionic, non-ionic or amphoteric, but best results are achieved using anionic polymeric suspending agents, preferably cross-linked. Cross-linked anionic polymers useful for the compositions and methods of the present invention include those that have one or more substituents such as carboxylate, carboxy acid anhydride, sulfonate, sulfate, and/or phosphate, which in contact with water ionize to form polymeric ions with a substantial plurality of negatively charged sites. Examples of suitable cross-linked anionic polymers include:
styrene acrylate/ammonium methacrylate copolymers;
styrene/acrylate copolymers;
styrene/maleic anhydride copolymers;
ethylene/maleic anhydride copolymers;
polyacrylic acid;
styrene/acrylate/acrylonitrile copolymers;
styrene/acrylonitrile copolymers;
poly(vinyl sulfate);
poly(methacrylic acid);
poly(sodium 4-styrenesulfonate);
polyacrylonitrile; and the like.

Suitable organic polymers include, for example, polymeric water-soluble polyelectrolytes preferably having a molecular weight of at least 150,000 and containing a substantially linear carbon chain backbone derived by the polymerization of an aliphatic unsaturated group. These polymers are polymeric organic substances which, when contacted with an aqueous medium, will form organic ions having a substantial number of ionizable groups distributed at a plurality of positions thereon.

One type of compound useful in the practice of the invention is the equimolar copolymer of a polycarboxylic acid derivative and at least one other monomer copolymerizable therewith. The polycarboxylic acid derivative may be maleic anhydride, maleic acid, iumaric acid, itaconic acid, citraconic acid, aconitic acid, the amides of these acids, the alkali metal, alkaline earth metal and ammonium salts of these acids, the partial alkyl esters, salts of the partial alkyl esters and the substituted amides of these polycarboxylic acids. The carboxylic acid, carboxylic acid salt, amide and substituted amide radicals are the ionizable groups which contribute to the hydrophilic properties and tend to make the polymers anionic. The corresponding derivatives of methacrylic crotonic or other polymerizable acids also are useful, for example, a copolymer of dialkyl maleate and acrylic acid.

When the hydrophilic maleic acid, acrylic acid, and the like derivatives are used, hydrophobic comonomers may be used, for example, ethylene, propylene, isobutylene, styrene, α-methylstyrene, vinyl acetate, vinyl chloride, vinyl formate, vinyl alkyl ethers, alkyl acrylates and alkyl methacrylates. In the practice of this invention the dibasic polybasic acid derivatives of the copolymers may be, for example, maleic acid, maleic anhydride, sodium maleate, potassium maleate, ammonium maleate, calcium maleate, monosodium maleate, monopotassium maleate, monoammonium maleate, monocalcium maleate, and a monoalkyl maleate, maleic acid amide, the partial amide of maleic acid, the N-alkyl substituted maleic acid amide, the N-amino ethyl maleamide, the N-aminoethyl maleimide, the alkylaminoalkyl maleamides, and the corresponding derivatives of itaconic, catraconic, fumaric and aconitic acids. Any of the above-identified polybasic acid derivatives may be copolymerized with any of the other monomers described above, and any other monomer which forms a copolymer with di-basic acid derivatives. The polybasic acid derivatives may be copolymerized with a plurality of comonomers.

Other suitable cross-linked, anionic polymers are the polymers of acrylic or methacrylic acid derivatives, for example, acrylic acid, the alkali metal and ammonium salts of acrylic acid, methacrylic acid, the alkali metal and ammonium salts of methacrylic acid, acrylamide, methacrylamide, the N-alkyl substituted amides, the N-aminoalkylamides, and the corresponding N-alkylaminoalkyl substituted amides, the aminoalkyl acrylates, the aminoalkyl methacrylamides and the Nalkyl substituted aminoalkyl esters of either acrylic or methacrylic acids. These polymeric compositions may be the homopolymers or they may be copolymers with other copolymerizing monomers such as ethylene, propylene, isobutylene, styrene, α-methylstyrene, vinyl acetate, vinyl formate, alkyl ethers, acrylonitrile, methacrylonitrile, vinyl chloride, vinylidene chloride, the alkyl acrylates, the alkyl methacrylates, the alkyl maleates, and the alkyl fumarates, and other olefinic monomers copolymerizable therewith.

Another class of cross-linked anionic organic polymers are the polymers of vinyl sulfonic acid, and the copolymers of vinyl sulfonic acid with one or more polymerizable organic monomers, for example, vinyl chloride, acrylonitrile, styrene, vinyl acetate and other polymerizable mono-olefinic compounds. The sulfonic acid groups so introduced may be converted to sulfonic acid salts, acid amides or other electrolytic groupings. The copolymers of this type may involve the use of a plurality of sulfonic acid monomers and/or a plurality of the conventional comonomers as described.

The cross-linked anionic polymers should have a weight average molecular weight of at least about 50,000, preferably at least about 150,000, and best results are achieved when the cross-linked anionic suspending agent has a weight average molecular weight of at least about 1,000,000.

Some compositions formulated in accordance with the present invention were studied using fourier transform infrared spectroscopy (FTIR). FTIR has been successfully employed as a sensitive probe for molecular structure and molecular interactions in numerous surfactant systems. Briefly, FTIR works because of the selective absorption of infrared radiation by molecular groups, resulting in stretching or bending vibrations within the molecules. Different functional groups within molecules (e.g. hydrocarbon groups or sulfate groups) absorb infrared radiation within well-known frequency ranges. Thus, the presence of certain functional groups can be identified. The specific frequency at which a group absorbs depends on the bond strengths and on local steric, electrostatic, and inductive effects. For example, the stretching frequency of $CH_2$ groups in hydrocarbon chains that are freely moving (as in a liquid) is much higher than the stretching frequency of $CH_2$ groups that are rigidly held (as in a solid).

FTIR is a probe for molecular structure and interaction, and has been used previously to study micelle and mixed micelle formation, order-disorder transitions in micelles and gels, and the solubilization of esters and long-chain alkanes into micelles. By following conformational changes in the hydrophobic chains and changes in the interactions of the ionic headgroups, the site of solubilization (i.e., the micelle core, surface or palisade layer) and the structural characteristics affecting solubilization can be determined.

The following studies directed to the compositions of the present invention were conducted using a cylindrical internal reflectance cell (CIRCLE) with a ZnSe reflectance element. This design allows material in water, a strong infrared absorber, to be examined. In addition, the cell can be thermostated over a range of temperatures.

In the studies, the infrared spectra of surfactant solutions containing a dimethicone silicone polymer were collected over a temperature range of 20°-50° C. with particular attention to the $CH_2$ stretching frequency (near 2920 cm−1).

Mixtures of 0.3 M ammonium lauryl sulfate (ALS) with very low levels of various cationic di-long chain alkyl nitrogen-containing compounds (a single long chain quat - cetrimonium chloride, two di-long chain quats-ADOGEN ® 432 (dicetyldimonium chloride) and AROSURF ®, and a tri-long chain quat-tricetylmonium chloride) with dimethicone were studied by FTIR in a closed internal reflectance cell between 25° C. and 45° C. The effect of temperature increase in these systems is to create more disorder in the acyl chains of ALS because of thermal agitation. This effect is reflected in small shifts of the C-H infrared stretching brands to higher frequency.

When AROSURF ® is present along with dimethicone, however, the $CH_2$ bands of ALS undergo a dramatic shift to lower frequency at about 30° C. and above. This shift suggests increased ordering of the ALS acyl chains, in opposition to the phase change normally associated with increased temperature. Without being bound by any particular theory, a possible explanation for this phenomenon is that the acyl chains of ALS are crowding together as silicone is solubilized into the micelle along the pallisade (rather than being solubilized in the core or around the outer region of the micelles). At the same time as the $CH_2$ shifts occur, a large increase in the area of the silicone infrared band occurs, suggesting that the silicone globules may be fragmenting into smaller pieces, a likely consequence of solubilization.

EXPERIMENTAL

Solutions: A mixture of an anionic and a cationic surfactant results in precipitation throughout a wide range of molar ratios. At extremely high molar ratios (anionic to cationic), however, no precipitation occurs The limit of the ALS to cationic ratio where no precipitation occurs was determined for monohexadecyltrimethylammonium chloride, (a single-long chain alkyl quaternary ammonium compound (quat)), dioctadecyldimethylammonium chloride, also called AROSURF ®, (a di-long chain alkyl $C_{18}$ quat) and trihexadecylmethylammonium chloride (a tri-long chain alkyl $C_{16}$ quat). The single long chain and tri-long chain alkyl quaternary ammonium nitrogen-containing compounds were unable to cause a lower frequency shift in acyl stretching bands.

0.30 M long chain alkyl sulfate surfactant solutions were mixed with the di-long chain alkyl quaternary ammonium nitrogen-containing compounds at molar ratio of at least 85:1 alkyl sulfate to quat so that no precipitation occurred. The two- and three-tailed quats are very insoluble in water, however, and solutions of these quats were prepared in isopropyl alcohol (IPA) sufficient to effect complete solubilization, and this solution was added to the long chain alkyl sulfate and/or ether sulfate surfactant(s). For comparison, IPA was also added to ALS when the long chain alkyl quaternary nitrogen containing compound was not present. The mixtures were sonicated for about one hour, silicone (dimethylpolysiloxane, also called dimethicone) was then added, and the mixture was sonicated again for about two hours to ensure good mixing. The mixtures were then centrifuged to separate out the excess silicone.

Infrared: Infrared analyses were performed on the solutions at controlled temperatures between 20° C. and 50° C. in a CIRCLE internal reflectance cell. Because of the high ratio of anionic surfactant to cationic quaternary ammonium nitrogen-containing compound (quat) the $CH_2$ bands include very little contribution from the quat, and shifts in these bands can be attributed essentially to the hydrocarbon chains of the anionic surfactant.

Solubility: Solutions of ALS, ALS/AROSURF ® and water (all with 5% IPA present) were prepared as above, and either 0.1 g eicosane or 0.2 ml of dimethicone-50 added, followed by sonication. The solutions then were placed in a 35° C. water bath and excess eicosane or dimethicone allowed to separate out by gravity for two hours. Aliquots of the solutions were taken for GC (eicosane) or GPC (silicone) analysis.

Figure 1:
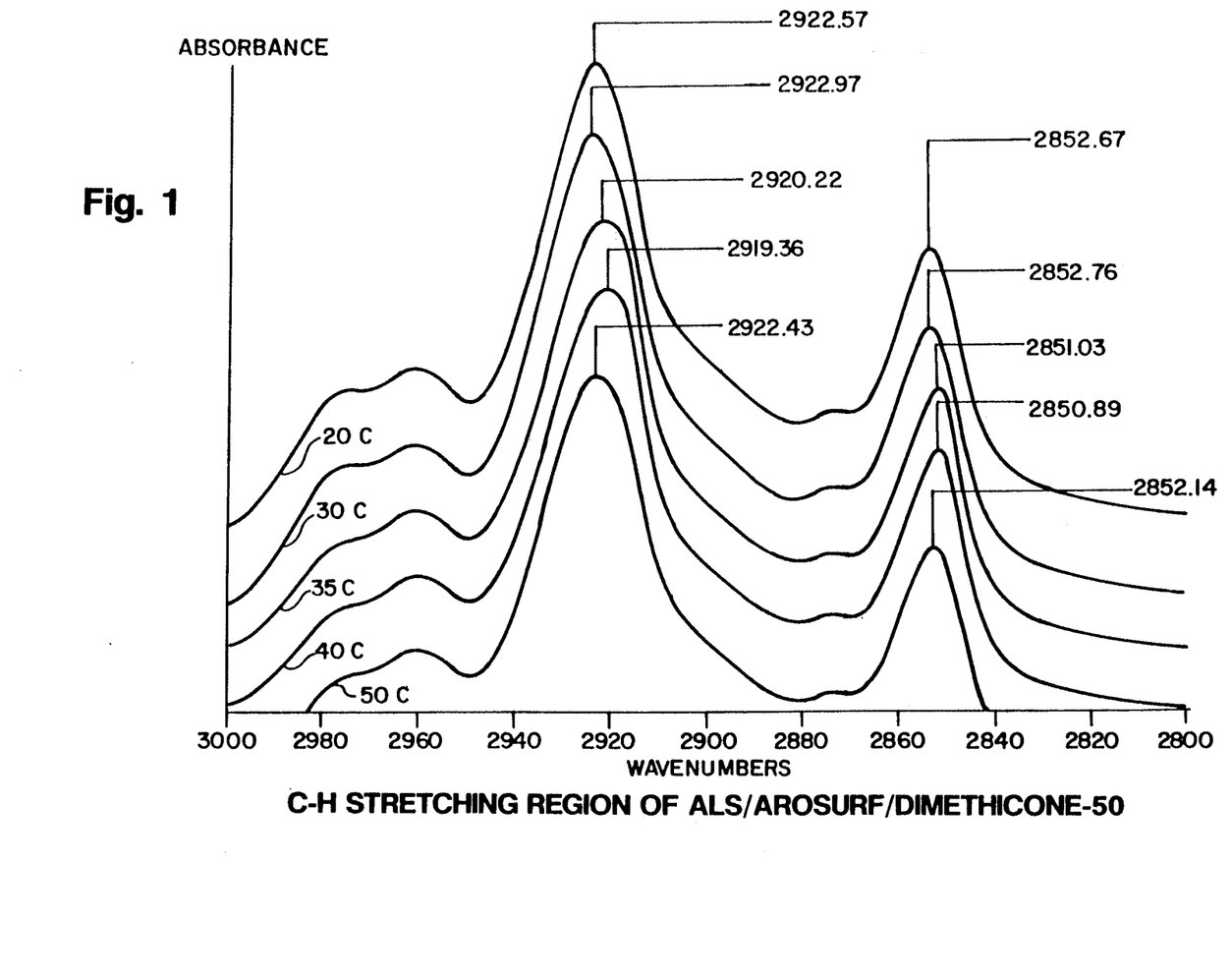
FIG. 1, shows infrared spectra for a composition containing ammonium lauryl sulfate and dioctadecyl ammonium chloride in a molar ratio of 120 to 1, together with dimethicone, showing the frequency shift of $CH_2$ peaks in the ammonium lauryl sulfate to a lower frequency at higher temperatures upwards from 30° C. until a reversal, occurring at 50° C.

The mixtures which were studied are listed in Table 1. The low-frequency shifts of the $CH_2$ stretching mode noted in Table 1 for several of the mixtures, and illustrated in FIG. 1 for ALS/AROSURF ®/dimethicone, occur as the temperature of the system is raised from 20° C. to 35° C. Above 35° C, the shift continues in some systems and reverses in others, as noted.

For a di-long chain C-18 quat in water, increasing temperature induces a phase change to a more disordered state, and a shift to higher frequency is observed for the $CH_2$ bands.

Figure 2:
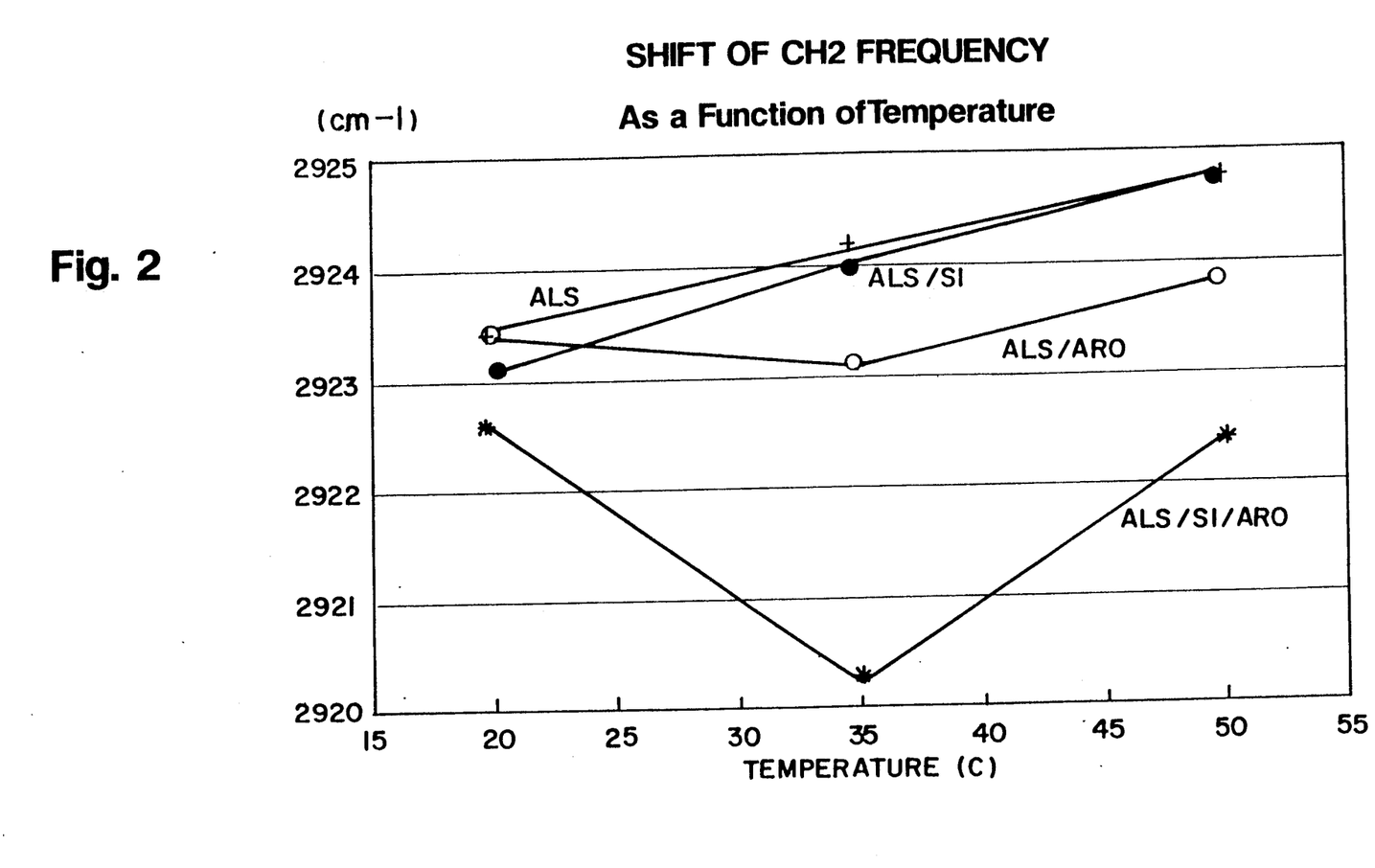
FIG. 2 is a graph of $CH_2$@ infrared stretching frequency vs. temperature for different surfactant systems with and without the di-long chain quaternary ammonium nitrogen-containing compound and with and without silicone showing the lowering of the ammonium lauryl sulfate $CH_2$ frequency peaks at higher temperatures for the combinations of long chain alkyl sulfate and di-long chain quaternary nitrogen-containing compound, with or without the silicone or other conditioning agents and the increase of the ALS $CH_2$ frequency peaks at higher temperatures for the ALS without quaternary, with and without the silicone or other conditioning agents.
Figure 3:
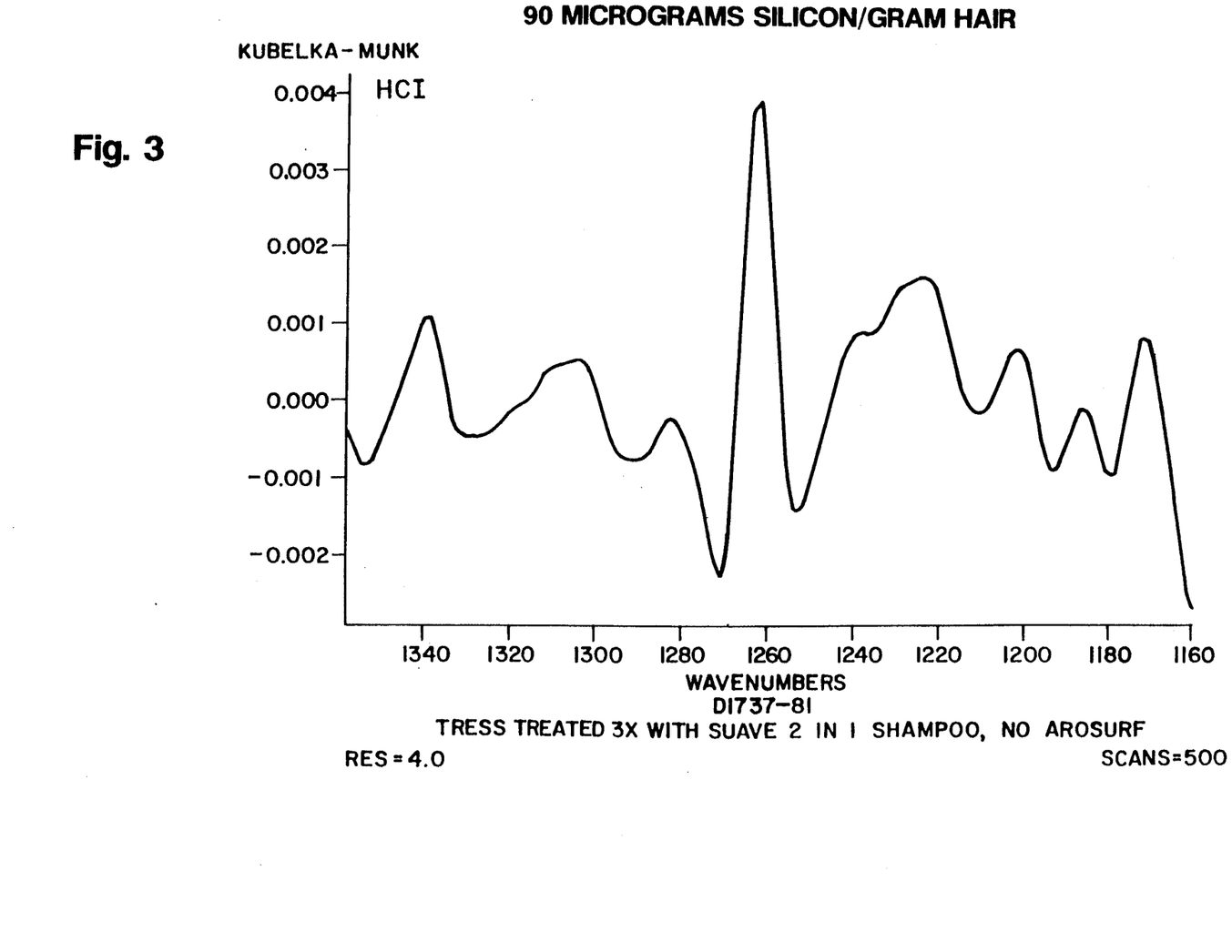
FIGS. 3 and 4 are graphs showing second derivative infrared spectra of hair treated with the composition described with reference to FIG. 1 with (FIG. 4) and without (FIG. 3) AROSURF ® wherein the intensity of the peak at 1261 $cm^{-1}$ corresponds to the amount of silicone conditioning agent deposited onto the hair. As shown, without the di-long chain quaternary nitrogen-containing compound, 90 micrograms of silicone was deposited vs. 115 micrograms of silicone deposited when the composition includes the di-long chain quaternary nitrogen-containing compound at a ratio of ALS to quaternary of 120:1.
Figure 4:
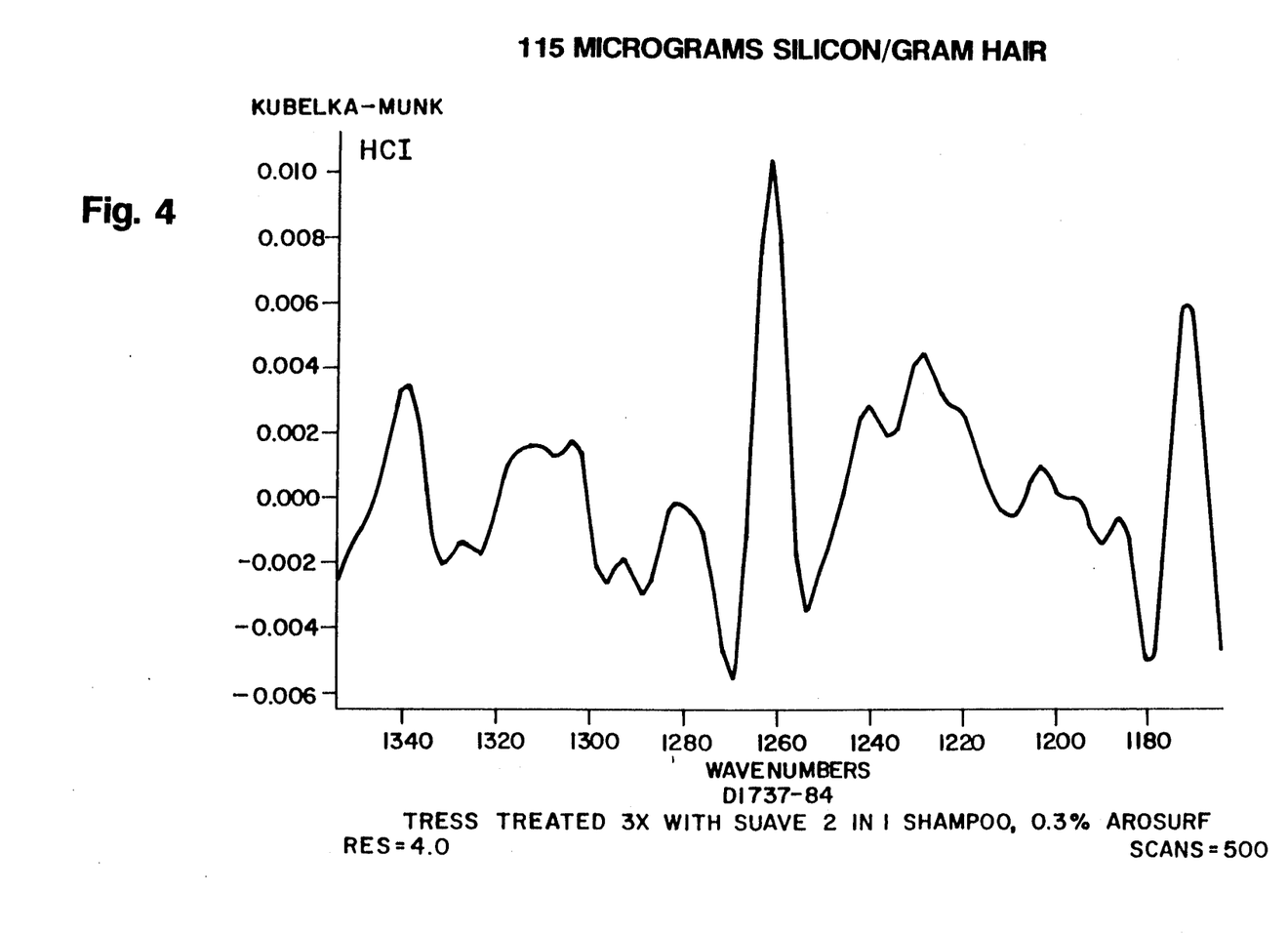

This phenomenon, temperature-induced disorder, is what is normally expected. In fact, this is what is observed for most of the systems studied, reflected in these experiments by shifts of the $CH_2$ stretching bands to higher frequency with temperature. It was unexpected that the ALS/AROSURF ® system (without silicone) showed a slight decrease in $CH_2$ frequency (FIG. 2). The low-frequency shift suggests the formation of a more ordered (micellar) system at higher temperatures.

It was further unexpected that with the addition of silicone, the low-frequency shift became more pronounced. This may be due to the presence of silicone molecules among the ALS hydrocarbon chains, causing increased crowding of the chains, and thus more ordering or rigidity and resulting in a lower frequency vibration of the $CH_2$ groups. Thus, silicone may be solubilized in the micelles.

In order to verify the suggestion of greater silicone solubilization, experiments were conducted to determine the solubility of eicosane (a C-20 hydrocarbon) and of dimethicone-50 in ALS and in ALS-/AROSURF ®. The results are shown in Table 2. The relative numbers are consistent; the ALS-/AROSURF ® system shows enhanced solubility for eicosane and dimethicone at 35° C.

The addition of AROSURF ® (a di-long chain C-18 quat) to ALS and/or ALES enhances the ability of the surfactant to solubilize non-polar compounds such as long chain hydrocarbons or low molecular weight silicone polymers at 30°-40° C.

TABLE 1

| SURFACTANT SYSTEM | LOW-FREQUENCY SHIFT OF CH$_2$ GROUP AT 35° C. |
|---|---|
| Ammonium Lauryl Sulfate | No |
| Ammonium Lauryl Sulfate/Si-50 | Yes |
| Ammonium Lauryl Sulfate/ distearyl dimonium chloride | (slight shift) |
| Ammonium Lauryl Sulfate/ distearyl dimonium chloride/ Si-50 | Yes |
| Ammonium Lauryl Sulfate/ distearyl dimonium chloride/ Si-350 | Yes |
| Ammonium Lauryl Sulfate/ distearyl dimonium chloride/ Si-1000 | Yes |
| Ammonium Lauryl Sulfate/ distearyl dimonium chloride/ Si-350 gum | No |
| Ammonium Lauryl Sulfate/ distearyl dimonium chloride/ cyclomethicone | Yes |
| SLS/distearyl dimonium chloride/ Si-50 | No |
| ALES-1/distearyl dimonium chloride/Si-50 | Yes |
| ALES-LDEA blend/ distearyl dimonium chloride/ Si-50 | Yes |
| Ammonium Lauryl Sulfate/ LDEA (1%)/distearyl dimonium chloride/Si-50 | Yes |
| Ammonium Lauryl Sulfate/ LDEA (2%)/distearyl dimonium chloride/Si-50 | Yes |
| Ammonium Lauryl Sulfate/MCAC | No |
| Ammonium Lauryl Sulfate/MCAC/ Si-50 | No |
| Ammonium Lauryl Sulfate/ adogen/Si-50 | No |
| Ammonium Lauryl Sulfate/TCAC | No |
| Ammonium Lauryl Sulfate/TCAC/ Si-50 | No |

*Si = dimethicone with a viscosity of 50, 350, or 1000 cs.
*LDEA = N,N-Bis(2-hydroxylethyl)-dodecanamide (lauramide diethanolamine)
*MCAC = - monohexadecyltrimethylammonium chloride
*TCAC = trihexadecylemthylammonium chloride

TABLE 2

| SOLUBILITY OF EICOSANE AND DIMETHICONE | | |
|---|---|---|
| Surfactant System | mg Eicosane/ml | mg Dimethicone/ml |
| Ammonium Lauryl sulfate/distearyl dimonium chloride | 1.4 | 120 |
| Ammonium Lauryl sulfate | 1.0 | 61 |
| water | 0.65 | 46 |

Examples of suitable shampoo compositions are set forth in Examples 1-6. Various additives such as alkali, foam boosters and viscosity modifiers can be added to these formulations to achieve a preferred pH of about 5.7 to 6.2 and a viscosity of about 3000 centipoises to about 5000 centipoises.

EXAMPLE 1

| | actual wt. % | moles |
|---|---|---|
| ammonium lauryl sulfate | 6.0 | .0211 |
| ammonium laureth sulfate (1 mole EO) | 10.0 | .0304 |
| distearyldimonium chloride (AROSURF ®) | 0.3 | .0005 |
| NaOH | 0.85 | |
| D & C Yellow #10 Dye | 0.0012 | |
| tetrasodium EDTA-water softener | 0.2 | |
| fragrance | 0.5 | |
| dimethylol dimethyl (DMDM) hydantoin (GLYDANT ®) preservative | 0.1 | |
| methyl and methylchloro isothiazolinone-preservatives | 0.05 | |
| soft water | QS to 100 | |

EXAMPLE 2

| | actual wt. % | moles |
|---|---|---|
| ammonium lauryl sulfate | 10.0 | .0351 |
| ammonium laureth sulfate (1 mole EO) | 6.0 | .0182 |
| distearyldimonium chloride (AROSURF ®) | 0.3 | .0005 |
| lauramide | 1.0 | |
| NaOH | 0.09 | |
| D & C Yellow #10 Dye | 0.0012 | |
| tetrasodium EDTA-water softener | 0.2 | |
| fragrance | 0.5 | |
| dimethylol dimethyl (DMDM) hydantoin (GLYDANT ®) preservative | 0.1 | |
| methyl and methylchloro isothiazolinone-preservatives | 0.05 | |
| soft water | QS to 100 | |

EXAMPLE 3

| | actual wt. % | moles |
|---|---|---|
| ammonium lauryl sulfate | 6.0 | .0211 |
| ammonium laureth sulfate (1 mole EO) | 10.0 | .0306 |
| distearyldimonium chloride (AROSURF ®) | 0.3 | .0005 |
| lauramide DEA | 1.0 | |
| NaOH | 0.085 | |
| D & C Yellow #10 Dye | 0.0012 | |
| tetrasodium EDTA-water softener | 0.2 | |
| fragrance | 0.5 | |
| dimethylol dimethyl (DMDM) hydantoin (GLYDANT ®) preservative | 0.1 | |
| methyl and methylchloro isothiazolinone-preservatives | 0.05 | |
| soft water | QS to 100 | |

EXAMPLE 4

| | actual wt. % | moles |
|---|---|---|
| ammonium laureth sulfate (1 mole EO) | 20.0 | .0608 |
| lauramide | 1.0 | |
| distearyldimonium chloride (AROSURF ®) | 0.3 | .0005 |
| NaOH | 0.08 | |
| D & C Yellow #10 Dye | 0.0012 | |
| tetrasodium EDTA-water softener | 0.2 | |
| fragrance | 0.5 | |
| dimethylol dimethyl hydantoin (GLYDANT ®) | 0.1 | |

-continued

|  | actual wt. % | moles |
|---|---|---|
| preservative |  |  |
| methyl and methylchloro isothiazolinone-preservatives | 0.05 |  |
| soft water | QS to 100 |  |

EXAMPLE 5

|  | actual wt. % | moles |
|---|---|---|
| ammonium lauryl sulfate | 6.0 | .0211 |
| ammonium laureth sulfate (5 moles EO) | 11.5 | .0228 |
| distearyldimonium chloride (AROSURF ®) | 0.3 | .0005 |
| NaOH | 0.09 |  |
| D & C Yellow #10 Dye | 0.0012 |  |
| tetrasodium EDTA-water softener | 0.2 |  |
| fragrance | 0.5 |  |
| dimethylol dimethyl hydantoin (GLYDANT ®) preservative | 0.1 |  |
| methyl and methylchloro isothiazolinone-preservatives | 0.05 |  |
| soft water | QS to 100 |  |

EXAMPLE 6

|  | actual wt. % | moles |
|---|---|---|
| ammonium laureth sulfate (10 moles EO) | 27.0 | .455 |
| lauramide | 1.0 |  |
| distearyldimonium chloride (AROSURF ®) | 0.3 | .0005 |
| NaOH | 0.085 |  |
| D & C Yellow #10 Dye | 0.0012 |  |
| tetrasodium EDTA-water softener | 0.2 |  |
| fragrance | 0.5 |  |
| dimethylol dimethyl hydantoin (GLYDANT ®) preservative | 0.1 |  |
| methyl and methylchloro isothiazolinone-preservatives | 0.05 |  |
| soft water | QS to 100 |  |

Examples of suitable conditioning shampoo compositions are set forth in Examples 7.

EXAMPLE 7

| ITEM | COMPONENT | WT. % | MOLES |
|---|---|---|---|
| 1 | ammonium lauryl sulfate | 6.0 | .0211 |
| 2 | ammonium laureth sulfate (1 mole EO) | 9.45 | .0287 |
| 3 | sodium lauryl sulfate | 4.5 | .0155 |
| 4 | distearyl dimethyl ammonium chloride (AROSURF ®) | 0.3 | .0005 |
| 5 | distearyl phthalamic acid | 3.5 |  |
| 6 | sodium hydroxide | 0.085 |  |
| 7 | F D & C Blue #1 | 0.00024 |  |
| 8 | D & C yellow #10 | 0.0012 |  |
| 9 | tetrasodium EDTA/ water softener | 0.2 |  |
| 10 | fragrance | 0.5 |  |
| 11 | DMDM hydantoin (GLYDANT ®) | 0.1 |  |

-continued

| ITEM | COMPONENT | WT. % | MOLES |
|---|---|---|---|
|  | preservative |  |  |
| 12 | methyl & methylchloro isothiazolinone-preservatives | 0.05 |  |
| 13 | 33% SE-30 polysiloxane gum/67% SF96-350 polysiloxane oil | 2.5 |  |
| 14 | soft water | QS to 100 |  |

MANUFACTURING STEPS: (Example 7)

Add items #1, #2, and #3 and begin heating batch to 180° F.–185° F.

At 180° F. add item #4 and allow to completely mix in.

Add items #5, allow to mix in.

Add item #6, #7, and #8.

Allow to mix for 30 minutes at 180° F.–185° F.

After this time, samples should be cooled with item #14.

The conditioning agent (item 13) then is added and the composition sonicated with good mixing at a temperature of at least 30° C. and preferably at 40° C. to 50° C. The composition at this point exhibits lower frequency stretching bands at the higher temperatures and the conditioning agent is easily dispersed or dissolved within the emulsion without separation.

EXAMPLE 8

| ITEM | COMPONENT | WT. % | MOLES |
|---|---|---|---|
| 1 | ammonium lauryl sulfate | 9.45 |  |
| 2 | ammonium laureth sulfate (1 mole EO) | 6.0 |  |
| 3 | lauramide | 1.1 |  |
| 4 | distearyl dimethyl ammonium chloride (AROSURF ®) | 0.3 |  |
| 5 | distearyl phthalamic acid (STEPMATE SC-1) | 3.5 |  |
| 6 | sodium hydroxide | 0.085 |  |
| 7 | tetrasodium EDTA | 0.2 |  |
| 8 | fragrance | 0.5 |  |
| 9 | DMDM hydantoin (GLYDANT ®) preservative | 0.1 |  |
| 10 | methyl & methylchloro isothiazolinone preservative | 0.05 |  |
| 11 | 33% SE-30 polysiloxane gum/67% SF96-350 polysiloxane oil | 2.5 |  |
| 12 | soft water | QS to 100 |  |

MANUFACTURING STEPS: (Example 8)

Add items #1, #2, and #3 and begin heating batch to 180° F.–185° F.

At 180° F. add item #4 and allow to completely mix in.

Add item #5 and allow to mix in.

Add item #6.

Allow to mix for 30 minutes at 180° F–185° F.

After this time, samples should be cooled with item #2.

EXAMPLE 9

| ITEM | COMPONENT | WT. % | MOLES |
|---|---|---|---|
| 1 | ammonium lauryl sulfate | 10.0 | |
| 2 | ammonium laureth sulfate (1 mole EO) | 4.0 | |
| 3 | sodium lauryl sulfate | 4.5 | |
| 4 | distearyl dimethyl ammonium chloride (AROSURF ®) | 0.2 | |
| 5 | distearyl phthalamic acid | 2.0 | |
| 6 | sodium hydroxide | 0.085 | |
| 7 | F D & C Blue #1 | 0.00035 | |
| 8 | D & C yellow #10 | 0.00120 | |
| 9 | tetrasodium EDTA/ water softener | 0.2 | |
| 10 | fragrance | 0.5 | |
| 11 | DMDM hydantoin (GLYDANT ®) preservative | 0.1 | |
| 12 | methyl & methylchloro isothiazolinone-preservatives | 0.05 | |
| 13 | 33% SE-30 polysiloxane gum/67% SF96-350 polysiloxane oil | 2.5 | |
| 14 | soft water | QS to 100 | |

EXAMPLE 10

| ITEM | COMPONENT | WT. % | MOLES |
|---|---|---|---|
| 1 | ammonium lauryl sulfate | 6.0 | |
| 2 | ammonium laureth sulfate (1 mole EO) | 9.45 | |
| 3 | sodium lauryl sulfate | 4.5 | |
| 4 | distearyl dimethyl ammonium chloride (AROSURF ®) | 0.3 | |
| 5 | distearyl phthalamic acid | 3.5 | |
| 6 | sodium hydroxide | 0.085 | |
| 7 | F D & C Blue #1 | 0.00024 | |
| 8 | D & C yellow #10 | 0.00120 | |
| 9 | tetrasodium EDTA/ water softener | 0.2 | |
| 10 | fragrance | 0.5 | |
| 11 | DMDM hydantoin (GLYDANT ®) preservative | 0.1 | |
| 12 | methyl & methylchloro isothiazolinone-preservatives | 0.05 | |
| 13 | Permethyl 101A | 5.0 | |
| 14 | soft water | QS to 100 | |

EXAMPLE 11

| ITEM | COMPONENT | WT. % | MOLES |
|---|---|---|---|
| 1 | ammonium lauryl sulfate | 9.45 | |
| 2 | ammonium laureth sulfate (1 mole EO) | 6.0 | |
| 3 | lauramide | 1.1 | |
| 4 | distearyl dimethyl ammonium chloride (AROSURF ®) | 0.3 | |
| 5 | distearyl phthalamic acid (STEPMATE SC-1) | 3.5 | |
| 6 | sodium hydroxide | 0.085 | |
| 7 | tetrasodium EDTA | 0.2 | |
| 8 | fragrance | 0.5 | |
| 9 | DMDM hydantoin (GLYDANT ®) preservative | 0.1 | |
| 10 | methyl & methylchloro isothiazolinone preservative | 0.05 | |
| 11 | eicosane | 3.0 | |
| 12 | soft water | QS to 100 | |

EXAMPLE 12

| ITEM | COMPONENT | WT. % | MOLES |
|---|---|---|---|
| 1 | ammonium lauryl sulfate | 9.45 | |
| 2 | ammonium laureth sulfate (1 mole EO) | 6.0 | |
| 3 | lauramide | 1.1 | |
| 4 | dibeehnyl dimethyl ammonium chloride (AROSURF ®) | 0.3 | |
| 5 | distearyl phthalamic acid (STEPMATE SC-1) | 3.5 | |
| 6 | sodium hydroxide | 0.085 | |
| 7 | tetrasodium EDTA | 0.2 | |
| 8 | fragrance | 0.5 | |
| 9 | DMDM hydantoin (GLYDANT ®) preservative | 0.1 | |
| 10 | methyl & methylchloro isothiazolinone preservative | 0.05 | |
| 11 | 33% SE-30 polysiloxane gum/67% SF96-350 polysiloxane oil | 2.5 | |
| 12 | soft water | QS to 100 | |

EXAMPLE 13

| ITEM | COMPONENT | WT. % | MOLES |
|---|---|---|---|
| 1 | ammonium lauryl sulfate | 9.45 | |
| 2 | ammonium laureth sulfate (1 mole EO) | 6.0 | |
| 3 | lauramide | 1.1 | |
| 4 | cetearyl dimethyl ammonium chloride (AROSURF ®) | 0.3 | |
| 5 | distearyl phthalamic acid (STEPMATE SC-1) | 3.5 | |
| 6 | sodium hydroxide | 0.085 | |
| 7 | tetrasodium EDTA | 0.2 | |
| 8 | fragrance | 0.5 | |
| 9 | DMDM hydantoin (GLYDANT ®) preservative | 0.1 | |
| 10 | methyl & methylchloro isothiazolinone preservative | 0.05 | |
| 11 | 33% SE-30 polysiloxane gum/67% SF96-350 polysiloxane oil | 2.5 | |
| 12 | soft water | QS to 100 | |

EXAMPLE 14

| ITEM | COMPONENT | WT. % | MOLES |
|---|---|---|---|
| 1 | ammonium lauryl sulfate | 9.45 | |
| 2 | ammonium laureth sulfate (1 mole EO) | 6.0 | |
| 3 | lauramide MEA | 1.1 | |
| 4 | dicoco dimethyl ammonium chloride (AROSURF ®) | 0.3 | |
| 5 | distearyl phthalamic | 3.5 | |

| ITEM | COMPONENT | WT. % | MOLES |
|------|-----------|-------|-------|
|      | acid (STEPMATE SC-1) |  |  |
| 6    | sodium hydroxide | 0.085 |  |
| 7    | tetrasodium EDTA | 0.2 |  |
| 8    | fragrance | 0.5 |  |
| 9    | DMDM hydantoin (GLYDANT ®) preservative | 0.1 |  |
| 10   | methyl & methylchloro isothiazolinone preservative | 0.05 |  |
| 11   | 33% SE-30 polysiloxane gum/67% SF96-350 polysiloxane oil | 2.5 |  |
| 12   | soft water | QS to 100 |  |

EXAMPLE 15

| ITEM | COMPONENT | WT. % | MOLES |
|------|-----------|-------|-------|
| 1    | ammonium lauryl sulfate | 9.45 |  |
| 2    | ammonium laureth sulfate (1 mole EO) | 6.0 |  |
| 3    | lauramide MEA | 1.1 |  |
| 4    | diarachidicdiethyl ammonium chloride | 0.3 |  |
| 5    | distearyl phthalamic acid (STEPMATE SC-1) | 3.5 |  |
| 6    | sodium hydroxide | 0.085 |  |
| 7    | tetrasodium EDTA | 0.2 |  |
| 8    | fragrance | 0.5 |  |
| 9    | DMDM hydantoin (GLYDANT ®) preservative | 0.1 |  |
| 10   | methyl & methylchloro isothiazolinone preservative | 0.05 |  |
| 11   | 33% SE-30 polysiloxane gum/67% SF96-350 polysiloxane oil | 2.5 |  |
| 12   | soft water | QS to 100 |  |

Other common cosmetic components and additives can be included in the compositions of the present invention, as long as the basic properties of the hair shampoos and shampoo-conditioners are not adversely affected. Such optional cosmetic components and additives include, but are not limited to, nonionic surfactants, amphoteric surfactants, fragrances, dyes, hair colorants, opacifiers, pearlescing agents, thickeners, dandruff control agents, hydrotropes, foam stabilizers, solubilizers, preservatives, water softening agents, acids, alkalis, buffers and the like. These optional components and additives usually are present in weight percentages of less than about 5% by weight each, and usually from about 0.1% to about 20% by weight of the composition in total.

For example, to improve consumer acceptance, both skin mildness and enhanced composition esthetics can be achieved by optionally including an amphoteric surfactant in the hair shampoo-conditioner in an amount rangeing from 0% to about 5% by weight of the composition.

Suitable amphoteric surfactants that can be included in the compositions of the present invention include, but are not limited to, betaines, hydroxypropylsultaines and amine oxides, or combinations thereof. Examples of amphoteric surfactants include, but are not limited to, cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate, or combinations thereof. A particularly useful amphoteric surfactant is cocamidopropyl betaine, sold commercially under the brandnames TEGO-GETAIN L10 and TEGO-BETAIN L7, by Goldschmidt Chemical Corp., Hopewell, Va. In general, however, any amphoteric surfactant can be included in the composition of the present invention as long as the stability, the conditioning and the cleansing efficiency of the composition are not adversely affected.

The hair shampoo-conditioner compositions of the present invention also can include nonionic surfactants to help impart esthetic, physical or cleansing properties to the composition. Likewise, the compositions can include other emulsifiers conditioning agents, inorganic salts, humectants and similar materials to provide the composition with desirable esthetic or physical properties. Generally, such optional ingredients are present in weight percentages of from about 0% to about 5% each, and from about 0% to about 20% in total, relative to the total weight of the composition.

The carrier of the hair shampoo-conditioner composition of the present invention is predominantly water, but nonaqueous solvents also can be included to help solubilize composition ingredients that are not sufficiently soluble in water, to adjust the viscosity of the composition or to act as a humectant. Suitable solvents include polyols, like glycerol; glycols, like ethylene glycol, propylene glycol and hexylene glycol; or mixtures thereof. The optional nonaqueous solvents should not adversely affect the ability of the composition to cleanse and condition the hair or adversely affect consumer appeal of the composition. A nonaqueous solvent can be present in the hair shampoo-conditioner composition of the present invention in an amount ranging from about 0% to about 5% by weight of the composition.

To achieve the full advantage of the present invention, the hair shampoo-conditioner composition is a relatively viscous mixture that is stable indefinitely at temperatures normally found in commercial product storage and shipping. A composition of the present invention, either opacified or pearlescent, is stable to phase separation and precipitation of composition ingredients at a temperature of about 20° C. to about 25° C. essentially indefinitely. The compositions also have demonstrated sufficient stability to phase separation or precipitation of ingredients at temperatures normally found in commercial product storage and shipping to remain unaffected for periods of one year or more.

What is claimed is:

1. A shampoo composition comprising an emulsion of water; an anionic cleaning surfactant selected from the group consisting of long chain ($C_{8-30}$) alkyl sulfates, alkyl ether sulfates and ethoxylated alkyl sulfates; and a di-long chain alkyl quaternary nitrogen-containing compound, wherein the two long alkyl chains bonded to the nitrogen atom have from about 12 to about 22 carbon atoms per alkyl chain and wherein the molar ratio of anionic cleaning surfactant to di-long chain alkyl quaternary nitrogen-containing compound is in the range of about 85 to 1 to about 1000 to 1.

2. The shampoo composition of claim 1 wherein the molar ratio of anionic cleaning surfactant to di-long chain alkyl quaternary nitrogen-containing compound is in the range of about 100–150 to 1.

3. The shampoo composition of claim 1 wherein said quaternary nitrogen-containing conditioning agent is selected from the group consisting of (a) compounds having only two long carbon chains and two identical or different short chain alkyl groups containing one to four carbon atoms bonded to the quaternary nitrogen atom, (b) compounds having two long carbon chains, one benzyl group and one short chain alkyl group having one to four carbon atoms bonded to the quaternary nitrogen atom, and (c) compounds having two long carbon chains, one hydrogen atom and one short chain alkyl group having one to four carbon atoms bonded to the quaternary nitrogen atom.

4. The composition of claim 1 wherein the di-long chain quaternary nitrogen-containing compound is a dioctadecyl quaternary ammonium salt.

5. The shampoo composition of claim 1 wherein the molar ratio of anionic cleaning surfactant to di-long chain alkyl quaternary nitrogen-containing compound is at least about 100 to 1.

6. The composition of claim 5 wherein the di-long chain quaternary nitrogen-containing compound is a dioctadecyl quaternary ammonium salt.

7. The shampoo composition of claim 1 wherein the composition is in the form of an emulsion and further includes a suspending agent in an amount of about 0.1% to about 5% by weight of the composition.

8. The composition of claim 7 wherein the suspending agent comprises a long chain phthalamic acid.

9. The composition of claim 8 wherein the suspending agent is distearyl phthalamic acid.

10. The composition of claim 9 further including a nonionic alkanolamide in an amount of about 0.1% to about 5% by weight of the composition.

11. A method of shampooing and conditioning hair which comprises applying to said hair the composition of claim 1.

12. A method of increasing the detergency action of lauryl sulfate and lauryl ether sulfate detergents in a shampoo composition at a hair washing temperature of at least about 30° C. comprising contacting the hair with the composition of claim 1 and rinsing the hair with water at a temperature of at least about 30° C.

13. The method of claim 12 wherein the hair is rinsed with water at a temperature of about 30° C. to about 45° C. to increase the capacity of the lauryl sulfate detergents to remove soil from the hair.

14. In a hair shampoo composition containing water, a long chain alkyl sulfate selected from the group consisting of long chain ($C_{8-30}$) alkyl sulfates, alkyl ether sulfates, and ethoxylated alkyl sulfates, a water-insoluble conditioning agent and a quaternary nitrogen-containing compound, the improvement comprising the quaternary nitrogen-containing compound having only two long chain alkyl groups bonded to the quaternary nitrogen atom, and in an amount such that the molar ratio of long chain alkyl sulfate to quaternary nitrogen-containing compound is in the range of about 85 to 1 to about 1000 to 1.

15. A method of shampooing and conditioning hair simultaneously which comprises applying to said hair the composition of claim 14.

16. A method of manufacturing the conditioning shampoo composition of claim 14, comprising:

mixing water; a long chain alkyl sulfate selected from the group consisting of long chain ($C_{8-30}$) alkyl sulfates, alkyl ether sulfates and ethoxylated alkyl sulfates, and a di-long chain alkyl quaternary ammonium nitrogen-containing compound in a molar ratio of long chain alkyl sulfate to quaternary nitrogen-containing compound of between about 85 to 1 and about 1000 to 1;

adding the water-insoluble conditioning agent to the mixture and heating the mixture to a temperature of at least 30° C.; and vigorously agitating the mixture to emulsify the conditioning agent in the composition.

17. A conditioning shampoo composition comprising an emulsion of water; about 0.5% to about 10% by weight of a water-insoluble conditioning agent; an anionic cleaning surfactant selected from the group consisting of long chain ($C_{8-30}$) alkyl sulfates, alkyl ether sulfates, and ethoxylated alkyl sulfates and a di-long chain alkyl quaternary nitrogen-containing compound containing only two long alkyl chains bonded to the nitrogen atom having from about 12 to about 22 carbon atoms per alkyl chain and wherein the molar ratio of anionic cleaning surfactant to di-long chain alkyl quaternary nitrogen-containing compound is in the range of about 85 to 1 to about 1000 to 1.

18. The conditioning shampoo composition of claim 17 wherein the molar ratio of anionic cleaning surfactant to di-long chain alkyl quaternary nitrogen-containing compound is at least about 100 to 1.

19. The conditioning shampoo composition of claim 17 wherein said quaternary nitrogen-containing conditioning agent is selected from the group consisting of (a) compounds having only two long carbon chains and two identical or different short chain alkyl groups containing one to four carbon atoms bonded to the quaternary nitrogen atom, (b) compounds having two long carbon chains, one benzyl group and one short chain alkyl group having one to four carbon atoms bonded to the quaternary nitrogen atom, and (c) compounds having two long carbon chains, one hydrogen atom and one short chain alkyl group having one to four carbon atoms bonded to the quaternary nitrogen atom.

20. The conditioning shampoo composition of claim 17 wherein the composition further includes an emulsifying agent in an amount of about 0.1% to about 5% by weight of the composition.

* * * * *